United States Patent [19]
Koenhen et al.

[11] Patent Number: 5,169,575
[45] Date of Patent: Dec. 8, 1992

[54] METHOD FOR PRODUCING A FLAT POROUS PRODUCT

[75] Inventors: Dirk M. Koenhen, Dedemsvaart; Hendrik D. W. Roesink, Hengelo, both of Netherlands

[73] Assignee: X-Flow B.V., Enschede, Netherlands

[21] Appl. No.: 642,214

[22] Filed: Jan. 16, 1991

[30] Foreign Application Priority Data

Jan. 17, 1990 [NL] Netherlands ............... 9000113

[51] Int. Cl.$^5$ .................................. B29C 67/20
[52] U.S. Cl. ........................... 264/41; 264/216
[58] Field of Search ................ 264/216, 41, 184

[56] References Cited

U.S. PATENT DOCUMENTS

3,922,470 11/1975 Amano et al. ............. 427/246 X
4,642,267 2/1987 Creasy et al. .................. 428/413

FOREIGN PATENT DOCUMENTS

0223415 5/1987 European Pat. Off. .
1953626 5/1971 Fed. Rep. of Germany .
1184571 3/1970 United Kingdom .
1187032 4/1970 United Kingdom .

*Primary Examiner*—Leo B. Tentoni
*Attorney, Agent, or Firm*—Young & Thompson

[57] ABSTRACT

The invention relates to a method for producing a flat porous product, in which a solution of an elastomeric material is deposited on a temporary substrate and the elastomeric material is coagulated on the substrate from the solution with the aid of a nonsolvent, wherein the surface of the substrate has an adhesion to the coagulating elastomer which is such that, after coagulation, the elastomeric flat product can be removed from the substrate without damage and the side (macroporous zone or bottom layer) of the elastomeric flat product facing the substrate possesses pores having a diameter in the region of 20–200 μm and has a porosity of more than 75%, a flat product which can be obtained according to this method for use as wound covering material and a method for treating wounds therewith.

12 Claims, No Drawings

METHOD FOR PRODUCING A FLAT POROUS PRODUCT

FIELD OF THE INVENTION

The invention relates to a method for producing a flat porous product, in which a solution of an elastomeric material is deposited on a temporary substrate and the elastomeric material is coagulated on the substrate from the solution with the aid of a nonsolvent.

BACKGROUND OF THE INVENTION

In membrane technology, porous films are made from polymer solutions by spreading a thin layer of polymer solution on a suitable flat bottom layer (substrate), for example a glass plate. The bottom layer is then immersed together with the polymer solution in a nonsolvent for the polymer. The polymer solution will separate (precipitate), and this results in a particular porous structure in the polymeric material which has then solidified. This process is termed coagulation. After coagulation, the membrane can be removed from the glass plate and used as is. This method is in principle much used for producing reverse osmosis and ultrafiltration membranes, in particular of nonelastomeric polymers.

A specific membrane having a strongly asymmetrical structure and suitable for use as a wound covering material (artificial skin) is described in the Dutch Patent Application NL-A-8801741, which corresponds to a considerable extent to EP-A-0,351,016 (publication date Jan. 17, 1990). The wound covering material has a gradient in the pore size distribution viewed in the cross section of the material, and this implies that there is a top layer which is in contact with the environment and possesses pores of less than 0.5 μm, while the side which is in contact with the damaged skin (bottom layer) possesses relatively large pores in the region of 20-200 μm. The wound covering material is produced by a method in which the starting point is a polymer solution (preferably polyurethanes) to which particles (for example salt particles) have been added. These solid particles have a twofold purpose. Firstly, they serve to prevent shrinkage phenomena which occur during and shortly after the coagulation process; secondly they serve as so-called pore formers. The relatively large pores in the bottom layer are obtained by adding particles with the correct dimensions to the polymer solution. These particles which are washed out, after coagulation of the polymer solution, using a solvent suitable for said particles, therefore leave behind pores having a particular size and, in addition, prevent shrinkage phenomena in the precipitating polymer solution. It will be clear that the solvent used for washing out has to be an agent other than the coagulating medium for the polymer solution so that the particles are not already washed out in the coagulating medium. The polymer therefore has first to be precipitated and then the salt particles still present have to be washed out. Suitable particles are, for example, crystals of the salt sodium citrate. The thin top layer having the small pores present therein can be obtained from a similar solution (but now without salt crystals).

The method described is very time-consuming and is only suitable for obtaining small surfaces (a few cm$^2$) of the wound covering described on a laboratory scale. The very thin top layer (thickness 0.01-0.2 mm) is very difficult to apply, while the use of two different nonsolvents also presents very many production problems.

The use of elastomeric materials for producing imitation leather is also known from the literature. An important property of imitation leather is the permeability to water vapour, the material nevertheless having to have the necessary mechanical strength. Imitation leather can also be made by starting from a polymer solution and a coagulation process in which a product is eventually obtained which is composed of two layers: a thin layer having small pores is applied to a porous carrier and eventually forms an integral whole with said porous carrier. The pore size in the porous carrier layer is in general not larger than a few micrometers, while the pore size in the top layer is not described. It will be clear that, in view of the applications of imitation leather, the microporous top layer has to have a very good and lasting adherence to the porous substrate layer.

The problem underlying the present invention was to provide a method for producing a flat porous product which is suitable, for example, as wound covering material, which method can in principle be carried out in one step, the use of two different nonsolvents being avoided and the desired pore structure nevertheless being obtained.

This problem is solved according to the invention.

SUMMARY OF THE INVENTION

The invention relates to a method for producing a flat porous product, in which a solution of an elastomeric material is deposited on a temporary substrate and the elastomeric material is coagulated on the substrate from the solution with the aid of a nonsolvent, wherein the surface of the substrate has an adhesion to the coagulating elastomer which is such that, after coagulation, the elastomeric flat product can be removed from the substrate without damage and the side (macroporous zone or bottom layer) of the elastomeric sheet facing the substrate possesses pores having a diameter in the region of 20-200 μm and has a porosity of more than 75%.

DETAILED DESCRIPTION OF THE INVENTION

In the method according to the invention, smaller pores, for example pores having a diameter of 0.1-25 μm, preferably 1-20 μm, may be present in the walls of the pores having a diameter of 20-200 μm.

In order to obtain the desired pore structure in the bottom layer of the flat product, the use of a solution having a relatively low polymer concentration is necessary. In general, the elastomer concentration of the solution should not exceed 18% by weight, referred to the total solution. Preferably, the elastomer concentration is even lower than 10% by weight.

The invention is based on the principle that an elastomeric sheet having desired pore sizes can be obtained by spreading a dilute polymer solution on a substrate layer which has a porosity or surface roughness such that shrinkage of the polymer during or after coagulation is prevented, in particular in a manner such that the intended structure is obtained. After coagulation and possible post-treatments, it is possible to remove the elastomeric flat product once produced from the temporary carrier layer (substrate) used, without damaging the elastomeric flat product. According to the method of the present application, it is possible to produce the wound covering materials described in NL-A-8801741 or EP-A-0,351,016 by a one-step process. It is also still possible, however, to produce a wound covering composed of more than one layer by the method according to the invention.

With respect to the temporary substrate used in the method according to the invention, two parameters play an important part.

The physical or chemical structure of the material. The structure of the temporary carrier is such that the usual shrinkage during the coagulation of the elastomeric polymer solution is prevented or counteracted.

The permeability of the material to the coagulant.

An important aspect of the present invention is the fact that the desired porous structure (including the so-called micropores in the walls of the pores of the macroporous zone or bottom layer) cannot be obtained if the separation of the bottom layer is started by the coagulating medium which reaches said bottom layer via the temporary support layer. The desired situation is therefore that the separation is initiated in the bottom layer by the coagulating medium which has travelled through the polymeric film, originating from the top of the deposited polymeric film.

In the method according to the invention, it is preferable to use water as nonsolvent or coagulating medium.

A very important advantage of the invention is that a flat porous product is obtained which detaches from the temporary carrier in a manner such that the unshrunken structure initially present remains unchanged and the product can be used as a wound covering material. It is important that, during the coagulation and possible post-treatment, the coagulated polymeric layer continues to adhere well to the temporary carrier layer or support layer.

In the method according to the invention, the substrate used can be a material which yields the intended structure of the elastomeric flat product. In particular a woven or nonwoven material of cellulose, polypropene, polyethene and/or polyester is used as substrate. It is also possible, however, to use as substrate an impermeable sheet or plate whose surface has been roughened, for example by means of a corona treatment.

It is not readily possible to define unambiguously the nature of the surface of the substrate which is used in the method according to the invention. Nevertheless, the adhesion of the elastomeric flat product to the substrate can be quantified in various ways. For porous support layers, use can be made of the weight per m$^2$ since the amount of fibrous material per unit surface area can be regarded as a measure of the porosity. In the case of a nonwoven polyester material, reference may be made here to the materials Viledon F0 2402 and Viledon F0 2406 (cf. the examples). The adhesion of the elastomeric flat product (for example Pellethane 2363) to Viledon F0 2402 is too strong and to Viledon F0 2406 it is good. Viledon F0 2402—weight 85 g/m$^2$, permeability to air 250 dm$^3$/s.m$^2$ at 2 mbar. Viledon F0 2406—weight 180 g/m$^2$, permeability to air 10 dm$^3$/s.m$^2$ at 2 mbar.

Another and more general way of quantifying can be borrowed from the adhesive tape industry. The following standard procedure may be used:

The elastomeric flat product projects 10 mm at one side on a strip of the support layer having a length of 250 mm with an elastomeric flat product applied to it. The width of the test strip is 25 mm. The condition of the elastomeric flat product is such that it can be used as a wound covering material. The temperature is 21°–25° C. and the relative atmospheric humidity 25–55%. The wound covering is removed gradually. The force with which this is done must be constant and not less than 1N over a length of 125 mm. The force must not, however, exceed a value of 30N.

The elastomeric flat product produced by the method of the invention preferably possesses pores having a diameter of not more than 0.7 μm, preferably 0.1–0.5 μm, at the side (microporous zone, top layer) facing away from the substrate. These pores in the top layer of the elastomeric flat product can be formed by bringing the elastomeric flat product into contact with vapour of a nonsolvent, preferably water, before coagulation.

Surprisingly, it has been found that adding a hydrophilic polymer to the solution of the elastomeric material yields an elastomeric flat product which is more hydrophilic than can be expected on the basis of the properties of the starting materials. As hydrophilic polymers, mention may be made here of polyacrylic acid, polyvinyl alcohol, polyvinyl acetate, polyvinylpyrrolidone, polyethylene glycol, polyvinylpyridine, polyethyleneimine etc. Excellent results are obtained, however, if polyvinylpyrrolidone is used as a hydrophilic polymer.

The amount of hydrophilic polymer depends strongly on the concentration of the elastomer in the solution. In general, the amount of the hydrophilic polymer will be 1–20% by weight, referred to the elastomer.

For the use as a wound covering material, the hydrophilic nature of the elastomer has advantages in relation to the water transport from the damaged skin covered (wound), and the acceptance of the wound covering material by the wound, and in relation to avoiding adsorption of, for example, protein which could block the small pores in the top layer.

The invention also relates to a flat product which can be obtained by the method described above and is suitable for use as a wound covering material which may have a thickness, for example, of 10–500 μm.

The invention also relates to the use of such a flat product in the field of pharmacy, medicine or cosmetics. Thus, the invention also relates to a method for treating wounds which is characterised in that a flat product which can be obtained by the method of the invention is used in the process.

In the following examples, which must not be interpreted as restrictive, the invention is explained in greater detail.

COMPARATIVE EXAMPLE 1

A solution of 10 g of polyether urethane (Pellethane 2363; DOW Chemical) in 100 g of N-methylpyrrolidone to which 1 g of lithium chloride (which is used to increase the solubility of the polymer) has been added was spread on a clean glass plate having a thickness of 0.4 mm using a so-called "doctor knife". The glass plate with the polymer solution on it was then immersed in a water bath (temperature 45° C.). The film produced separated from the glass plate even during the coagulation of the polymer solution and exhibited a shrinkage exceeding 200%, No. 20–200 μm pores could be detected in the bottom layer. The elastomeric flat product shrivelled up completely during drying after complete coagulation, and this also indicates unduly small pores in the bottom layer.

EXAMPLE I

The solution prepared in accordance with Comparative Example 1 was spread on a nonwoven polyester support layer (Viledon FO 2406) in the same thickness and was then immersed in a water bath (temperature 45° C.). The elastomeric flat product now continued to adhere to the porous nonwoven during and after coagulation and exhibited no shrinkage. After complete coagulation and removal of the support layer, it was possible to dry the elastomeric flat product normally and 20–200 µm pores were found in the bottom layer. After examination with the scanning electron microscope (SEM examination) it was also found that the walls of the large pores possessed still smaller pores which are able to serve as adhesion points.

COMPARATIVE EXAMPLE 2

A solution from Comparative Example 1 was spread on another type (more open; see explanation in the text) of polyester nonwoven (Viledon F 2402) and was processed further in the same way. After complete coagulation, it was found that the elastomeric flat product was very difficult to remove from the support layer without damaging it. In addition, after SEM examination it was found that there were few to no large pores (20–200 µm) present in the bottom layer. These effects are attributed to the fact that, in the first place, the polymer solution can penetrate too far into the porous nonwoven (result-unduly strong adhesion!) and that water (coagulant) also penetrates from the rear side at the same time, as a result of which coagulation can also take place starting from the rear side, with the result that the structure desired for a wound covering is not obtained.

EXAMPLE II

A polymer solution containing 10 g of polyether urethane (Pellethane 2363), 100 g of N-methylpyrrolidone and 3.3 g of polyvinylpyrrolidone was spread on a polyester nonwoven (Viledon FO 2406) and passed in the course of 10 seconds through a zone of water vapour saturated at 45° C. and then immersed in a 45° C. water bath. After coagulation, it was found that a wound covering had been produced which had a thin top layer possessing approximately 0.1–0.5 µm pores and a bottom layer possessing 20–200 µm pores. After rinsing out and drying, this elastomeric flat product was found to be markedly more hydrophilic than a specimen made without adding PVP to the polymer solution. Such an experiment carried out on a polypropylene nonwoven (AWA 17) revealed corresponding results.

COMPARATIVE EXAMPLE 3

A polymer solution prepared in accordance with Example II was spread on a smooth, nonporous polypropylene sheet and processed further identically to Example II. Even during the coagulation the elastomeric flat product separated from the sheet and a large shrinkage occurred, with the result that the resultant material could no longer be used as an elastomeric flat product.

EXAMPLE III

A solution in accordance with Example II was spread on a nonporous polypropylene sheet having a surface which had been modified by corona treatment. No shrinkage now occurred and the resultant artificial skin had the same properties as that of Example II.

We claim:

1. Method for producing a flat porous product which comprises: depositing a solution of an elastomeric material on a temporary substrate, coagulating the elastomeric material on the substrate from the solution with the aid of a non-solvent so as to obtain said flat porous product, said substrate possessing a surface having an adhesion with respect to the flat porous product which is not damaging thereto upon removal thereof from said substrate, said flat porous product having a macroporous zone facing the substrate which possesses pores having a diameter in the range of 0.1–200 µm and a porosity of more than 75%.

2. Method according to claim 1, wherein the macroporous zone possesses pores having a diameter of 1–20 µm.

3. Method according to claim 2, wherein the solution used has a concentration of not more than 18% by weight of elastomeric material.

4. Method according to claim 1, wherein water is used as the non-solvent.

5. Method according to claim 1, wherein a hydrophilic polymer selected from the group consisting of polyacrylic acid, polyvinyl alcohol, polyvinyl acetate, polyvinylpyrrolidone, polyethylene glycol, polyvinylpyridine, and polyethyleneimine is added to the solution in an amount of 1–20% by weight of elastomeric material.

6. Method according to claim 5, wherein the hydrophilic polymer is polyvinylpyrrolidone.

7. Method according to claim 1, wherein the substrate is a woven or non-woven material selected from the group consisting of cellulose, polypropene, polyethene, and polyester.

8. Method according to claim 1, wherein the flat porous product has a microporous zone facing away from the substrate, said microporous zone possessing pores having a diameter of not more than 0.7 µm.

9. Method according to claim 8, wherein the microporous zone possesses pores having a diameter of 0.1–0.5 µm.

10. Method according to claim 8, wherein the pores in the microporous zone are formed by contacting the elastomeric material with vapor of a non-solvent before coagulation.

11. Method according to claim 10, wherein the elastomeric material is contacted before coagulation with water vapor.

12. Method according to claim 1, wherein the substrate has a surface adhesion with respect to the flat porous product which is sufficiently strong to prevent shrinkage of the flat porous product obtained during coagulation.

* * * * *